(12) United States Patent
Pettit

(10) Patent No.: US 7,286,210 B2
(45) Date of Patent: Oct. 23, 2007

(54) PASSIVE OPTICAL SENSOR USING CARBON NANOTUBES

(76) Inventor: John W. Pettit, 7808 Potters Mill Ct., Rockville, MD (US) 20855

( * ) Notice: Subject to any disclaimer, the term of this patent is extended or adjusted under 35 U.S.C. 154(b) by 0 days.

(21) Appl. No.: 11/024,406

(22) Filed: Dec. 30, 2004

(65) Prior Publication Data

US 2005/0248768 A1    Nov. 10, 2005

Related U.S. Application Data

(60) Provisional application No. 60/533,147, filed on Dec. 31, 2003.

(51) Int. Cl.
*G01L 7/00* (2006.01)
(52) U.S. Cl. ............... 356/32; 356/432; 356/445; 73/800
(58) Field of Classification Search .......... 356/32, 356/445, 432; 73/800
See application file for complete search history.

(56) References Cited

U.S. PATENT DOCUMENTS

| | | | |
|---|---|---|---|
| 6,108,081 A * | 8/2000 | Holtom et al. | 356/301 |
| 6,203,864 B1 * | 3/2001 | Zhang et al. | 427/592 |
| 6,848,320 B2 * | 2/2005 | Miyajima et al. | 73/763 |
| 2004/0188780 A1 * | 9/2004 | Kurtz | 257/414 |

OTHER PUBLICATIONS

Zhao et al, "Direction-sensitive Stress Measurements with Carbon Nanotube Sensors", Polymers for Advanced Technologies, vol. 13, 759-764 (2002) □□.*

Wood et al, "Single-wall carbon nanotubes as molecular pressure sensors", Applied Physics Letters, vol. 76. No. 20 (May 15 2000), pp. 2883-2885.*

"Pressure Dependence of Optical Transitions in Semiconducting Single-Walled Carbon Nanotubes", W. Shan, et al., Phys. Stat. Sol. (b) 241, No. 14, Oct. 27, 2004, pp. 3367-3373.

"Nanotube Light-Controlled Electronic Switch", S. Rotkin, et al., International Journal of Nanoscience, vol. 1, Nos. 3 and 4 (2002), pp. 347-355.

"Band Gap Fluoresence from Individual Single-Walled Carbon Nanotubes", M. O'Connell, et al., Science, vol. 297, Jul. 26, 2002, pp. 593-596.

"Electrically Induced Optical Emission from a Carbon Nanotube FET", J. Misewich, et al., Science, vol. 300, May 2, 2003, pp. 783-786.

"Carbon Nanotube Single Electron Transistor with Ultra-High Sensitivity for Optical and Bio-Sensor", K. Matsumoto, Osaka University, Japan, (2003).

"Interactions Between Conjugated Polymers and Single-Walled Carbon Nanotubes", D. Steuerman, et al., J. Phys. Chem., B 2002, 106, pp. 3124-3130.

(Continued)

*Primary Examiner*—Richard A. Rosenberger
(74) *Attorney, Agent, or Firm*—Blank Rome LLP

(57) ABSTRACT

A passive optical sensor operates independently of light amplitude by using a semiconducting carbon nanotube material. The material has an optical property dependent on wavelength, e.g., wavelength of absorption, ratio of absorptions at two wavelengths, or fluorescence at one wavelength in response to light at another wavelength. The property is changed by compressing the material or exposing the material to a charge. Light is passed through the material so that the change in the property can be detected.

40 Claims, 2 Drawing Sheets

OTHER PUBLICATIONS

"Functionalized Surfaces Based on Polymers and Carbon Nanotubes for Some Biomedical and Optoelectronic Applications", L. Dai, et al., Institute of Physics Publishing, Nanotechnology 14 (2003), pp. 1081-1097.

"Nanotube Optoelectronic Memory Devices", A. Star, et al., American Chemical Society, 2004, Nano Letters, vol. 4, No. 9, pp. 1587-1591.

"Extraordinary Mobility in Semiconducting Carbon Nanotubes", T. Durkop, et al., American Chemical Society, 2004, Nano Letters, vol. 4, No. 1, pp. 35-39.

"Water-Soluble and Optically pH-Sensitive Single-Walled Carbon Nanotubes from Surface Modification", W. Zhao, et al., J. Am. Chem. Soc., 2002, pp. 12418-12419.

"Switching Behavior of Semiconducting Carbon Nanotubes Under An External Electric Field", A. Rochefort, et al., Applied Physics Letters, vol. 78, no. 17, Apr. 23, 2001, pp. 2521-2523.

"High Performance Electrolyte-Gated Carbon Nanotube Transistors", S. Rosenblatt, et al., pp. 1-12 (2002).

Carbon Nanotube Chemical and Mechanical Sensors:, S. Peng, et al., Conference Paper for 3rd International Workshop on Structural Health Monitoring, pp. 1-8 (2001).

"Quantitative Analysis of Optical Spectra from Individual Single-Wall Carbon Nanotubes", A. Hagen, et al., Dept. of Physical Chemistry, Germany, Nano Letters in Press, pp. 1-6 (2003).

"Variable and Reversible Quantum Structures on a Single Carbon Nanotube", C. Kilic, et al., Nov. 17, 2000, pp. 1-7.

"Fullerene Nanotubes in Electric Fields", L. Lou, et al., Physical Review B, vol. 52, No. 3, Jul. 15, 1995.

"Reversible Band Gap Engineering in Carbon Nanotubes by Radial Deformation", O. Gulseren, et al., Mar. 11, 2002, pp. 1-8.

"Nano Electro Mechanics of Semiconducting Carbon Nanotube", S. Peng, et al., Journal of Applied Mechanics, Jul. 2002, vol. 69, pp. 451-453.

* cited by examiner

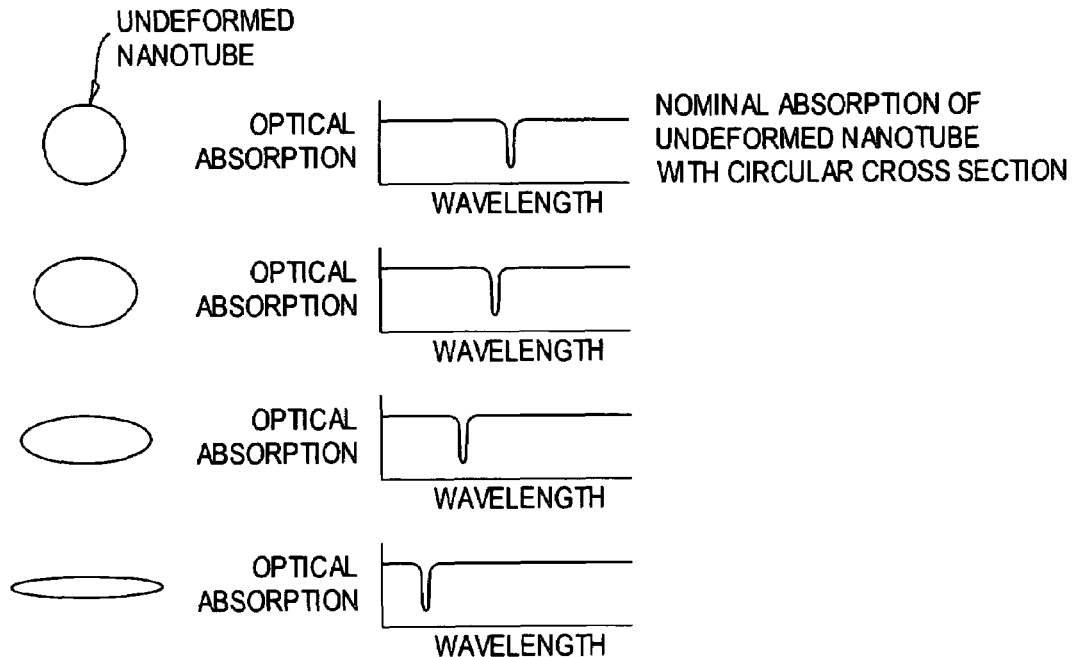
FIG. 1 OPTICAL ABSORPTION OF NANOTUBE VERSUS OPTICAL WAVELENGTH FOR SEVERAL CASES OF DEFORMATION
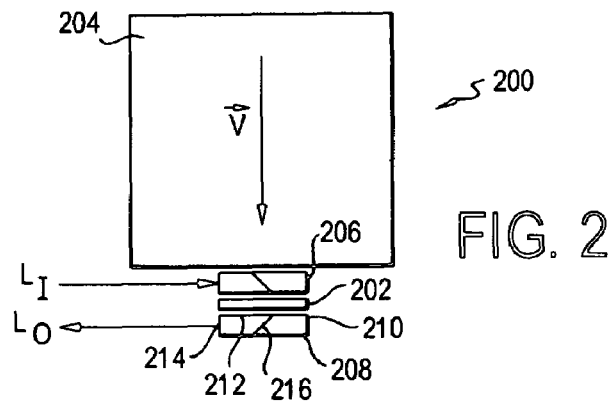
FIG. 2
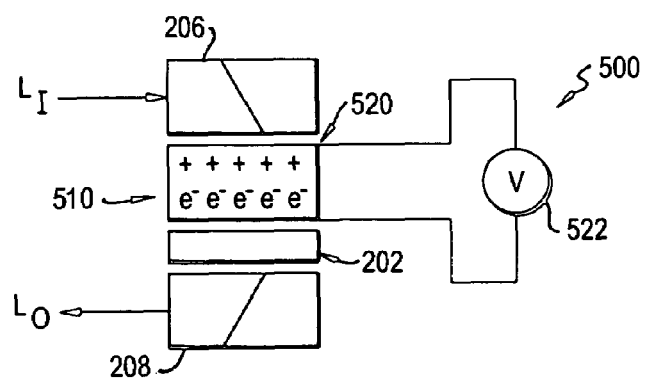
FIG. 5

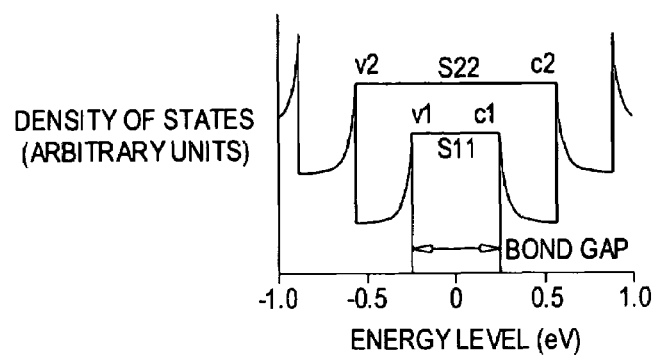
FIG. 3
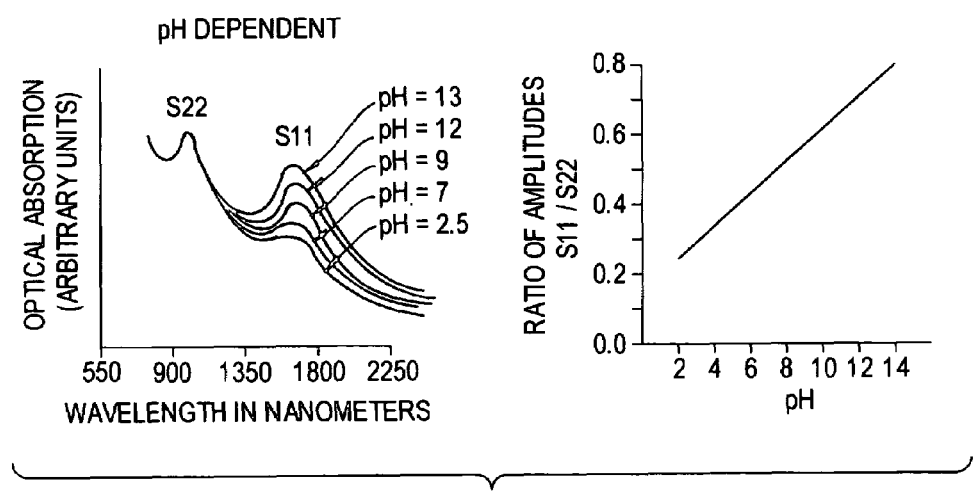
FIG. 4  OPTICAL ABSORPTION MODULATION OF NANOTUBES DUE TO FERMI LEVEL MODULATION

PASSIVE OPTICAL SENSOR USING CARBON NANOTUBES

REFERENCE TO RELATED APPLICATION

The present application claims the benefit of U.S. Provisional Patent Application No. 60/533,147, filed Dec. 31, 2003, whose disclosure is hereby incorporated by reference in its entirety into the present disclosure.

FIELD OF THE INVENTION

The present invention is directed to a passive optical sensor and more particularly to a passive optical sensor which operates by causing a wavelength-dependent change in the optical characteristics of a carbon nanotube material.

DESCRIPTION OF RELATED ART

Fiber optic networks are being developed by the US Air Force and the aerospace industry to control future aircraft in what has been termed the "Fly-by-Fiber" initiative. Essential to the operation of this passive fiber optic network are sensors that measure a variety of parameters required for flight control and other aircraft needs. These sensors must operate in a totally passive mode, where electrical power is not needed to be brought to the sensors. Furthermore, the sensors need to be compatible with the characteristics of wavelength division multiplexing, WDM, fiber optic networks. Lastly, but very importantly, the sensors need to be able to withstand very high levels of electromagnetic interference, EMI. These are a very challenging set of requirements that no other technology has been able to demonstrate a potential to meet.

The needs with respect to operability with WDM fiber optic networks are compounded by the additional requirements of operation in the harsh aircraft environment, field maintenance and service life. Sensors have to make a measurement of the physical parameter that they are intended to measure and place information regarding the value of that measurement onto the optical fiber in a manner that meets the WDM fiber optic network requirements just stated. In particular, information encoding methods that send information regarding the value that is being measured in the form of amplitude modulation of the light signal are not desired. This is mostly due to the fact that optical interconnections demonstrate dramatically variable amplitude losses. This gives rise to the need to recalibrate the system every time an optical connection is remade or when shock, vibration or strain changes the optical loss of a fiber optic connector. Such a recalibration requirement is unworkable in practice and is therefore unacceptable.

Simple sensors that work in a way that is light amplitude dependent would output an amount of light that is proportional to the value of the parameter being sensed. This light amplitude would be transmitted through the optical fiber and a detector would measure the light amplitude to obtain a signal that is representative of the parameter that was measured. This general technique has the problem that the light path through the optical network has to remain steady in that light losses cannot vary over time or through any other effects. This condition is almost never met in practical fiber optic networks, especially networks that operate on aircraft. For instance, typical fiber optic connectors can exhibit anywhere from a small fraction of a decibel loss to several decibels of loss, depending on the particular alignment, the buildup of dirt or grease and numerous other factors. This makes sensors that utilize light amplitude as their means of transmitting information not acceptable for this application.

In a different field of endeavor, carbon nanotubes are comprised of pure carbon that is in the form of a two dimensional sheet, termed graphene, that is rolled back upon itself to form a tubule or cylinder object with hemispherical end caps. The tubes are from about 0.3 nanometers to several nanometers in diameter, for the single walled variety, and up to approximately one millimeter in length. Tubes formed within tubes, termed multi-walled nanotubes, are also formed, and can have much greater diameters.

Carbon, the sixth element in the periodic table, is unique in nature and has many chemical forms and is the basis of life on earth. It forms covalent chemical bonds with itself and other elements that form into molecules, assemblages of atoms that have a definite size and shape. Most other elements in electronic or optical devices, such as silicon and metals, form ionic bonds that organize themselves into crystal structures that may grow to arbitrary size and shape, as they have no definite boundary as does a molecular structure.

The covalent bond that carbon forms in carbon nanotubes is what chemists call a hybrid orbital of the s orbital of one carbon atom and a p2 orbital of another carbon atom, resulting in an sp2 hybrid bond. This bond combines two carbon atoms at a 120 degree angle from one another and is flat, or two dimensional. Alternatively, carbon may combine with other carbon atoms in a sp3 hybrid bond that is a three dimensional tetrahedral structure. Diamond is an example of this structure. Interestingly, the sp2 hybrid bond in carbon nanotubes is stronger than the sp3 hybrid bond of diamond.

When a two dimensional sheet of carbon atoms held together in the sp2 hybrid bond form a tube, the normally flat bonds are stressed to accommodate the curvature of the tube. In nanotube literature, the nanotube is characterized in terms of its basis vectors, normally referred to by the indexes n, m that denote how far along each basis vector must be traveled to come back to the same point on the tube. Examples are 8,0 or 6,2 or 5,3 nanotubes. Although a complete discussion of the electronic band structure of nanotubes is rather complex, a simple intuitive view can be obtained by noting that the various amount of strain on the sp2 hybrid bond produced by nanotubes of varying n,m indexes causes among other things the gap between the valence band and the conduction band, termed the bandgap, to vary. Reference 6 below gives a thorough review of carbon nanotube band structure. When n=m, the bandgap vanishes and the nanotube is a metal. When n−m is evenly divisible by three, the bandgap is finite, but smaller than room temperature thermal energy of about 25 milli-electron volts. Therefore electrons can easily hop across the band gap due to thermal energies and these nanotubes are termed either semi-metals or simply metallic as well. All other nanotubes are semiconductors; their band gaps vary considerably, and have been found to be roughly proportional to the inverse of the nanotube diameter.

The actual population of allowed levels by electrons within a nanotube is described by the density of states, or DOS, equation. The density of states exhibits large spikes termed van Hove singularities. Optical transitions can take place between a van Hove singularity in the valence band and a van Hove singularity in the conduction band. In the case of a transition between the first van Hove singularity in the valence band to the first van Hove singularity in the conduction band, the optical transition is termed a V1 to C1, or sometimes an E11 or sometimes an S11 transition, depending on the author.

However, the properties of carbon nanotubes noted above have not yet been exploited in a passive optical sensor which can meet the above-noted requirements.

SUMMARY OF THE INVENTION

It will be seen that a need exists in the art to meet the requirements noted above for a passive optical sensor.

It is therefore an object of the invention to incorporate carbon nanotubes into a sensor so that the encoded information does not depend on the amplitude of the light.

It is another object of the invention to provide sensors which can provide completely passive optical operation of the entire network outside of a hardened central box where the computer processors, light sources and intelligent logic resides.

It is another object of the invention to provide sensors that need only enough light to be detected and yield an acceptable signal to noise ratio, but the specific light amplitude may vary considerably as long as this basic requirement is met and the information contained in the encoding technique will still give the correct measurement result.

To achieve the above and other objects, the present invention is directed to passive optical sensors which use carbon nanotubes to meet the requirements of "Fly-by-Fiber" WDM fiber optical networks as given above. These sensors are quite small and operate with no external supply of electrical power, and this is what is meant by a passive sensors. These sensors operate by means of light and thus are termed optical sensors, but they are intended to measure any physical parameter needed, such as voltage, current, magnetic field, temperature, pressure, oxygen or the presence of certain chemical or biological agents.

There are two related concepts that will be developed. Each concept provides the ability to transmit the information pertaining to the value of the parameter being measured without relying on the amplitude of the light signal going through the optical fiber.

The present invention senses a physical quantity by sensing a change in a wavelength-dependent optical characteristic (e.g., absorption or fluorescence) of carbon nanotubes caused by that physical quantity. The first technique utilizes a technique based on changing the exact wavelength at which a nanotube absorbs light as the technique to encode the information that is being sensed. The second technique compares light at two wavelengths (e.g., either absorption at those wavelengths or excitation and fluorescence).

With regard to the first technique mentioned above, it has been reviewed in the research literature that carbon nanotubes exhibit a phemonenon where their bandgap changes upon physical distortion, such as twisting or elongation or radial compression [References 7 through 10]. This effect is related to further stressing of the sp2 hybrid bonds as described above, in a simplified view of the effect of the physical distortion on the nanotube band structure. It has been shown that, in the case of a compressive radial distortion that has the effect of flattening the nanotube, a radial compression of about 22% for certain nanotubes causes the bandgap to completely close. The nanotube has then undergone a semiconductor to metallic transition. It was then shown that further distortion opened up the bandgap again, making for a metallic to semiconducting transition.

When a nanotube demonstrates an optical transition between, for instance, the first van Hove singularity in the valence band to the first van Hove singularity in the conduction band, this manifests itself as a narrow bandwidth absorption resonance in the optical transmission spectrum of the nanotube. The present inventor was the first to recognize, to his knowledge, that changing the nanotube bandgap also changes the distance between these two van Hove singularities and consequently changes the wavelength of the optical absorption of the nanotube. When the bandgap changes, so does the distance between the two van Hove singularities and the wavelength at which the optical absorption resonance changes accordingly. The only reference that marginally suggests this effect is Reference 5, where the optical spectra of nanotubes in micelles, or floating in surfactant solution was different from the optical spectra of nanotubes deposited onto a flat substrate. It was theorized by Axel Hagen and Tobias Hertel that the stresses on the nanotube were caused by imperfections in the substrate surface as the nanotube cling to the surface through van der Walls forces. This caused distortions in the nanotubes that may have altered the bandgap, but they did not actually say this in their research report [Reference 5]. Axel Hagen and Tobias Hertel estimated that this caused a blue shift in the nanotube spectra of about 65 nanometers and this seemed to be consistent with the published values of nanotube compressive modulus and the amount of strain that could reasonably be estimated from the surface imperfections.

The second technique is based on selective modulation of nanotube optical absorption. The Fermi level is the level to which electrons actually populate the allowed states in any given nanotube [Reference 6]. The Fermi level typically sits somewhere near the center of the bandgap in semiconducting nanotubes. Electrons can be either supplied to or taken away from the population of electrons in a nanotube by action of electric fields that are very near the nanotubes surface [References 2 through 4]. This has the effect of modulating the Fermi level in the nanotube. The phenomenon for this mechanism is called charge transfer doping and the electric field acts through what has been termed the "quantum capacitance" or sometimes the "chemical capacitance". This is another remarkable feature of carbon nanotubes. Electric fields acting very near the surface have a dramatic effect on nanotubes, so much so that single molecule sensors have been proposed based on this phenomenon. On the other hand externally generated electric fields have almost no effect on nanotubes [References 1-2] up to hundreds of millions of volts per meter. This gives the nanotubes the essential property of immunity from large amounts of EMI, which is a critical need for the Air Force.

In order for an optical absorption transition to take place an electron has to be present on the ground or relaxed state in order to take in the energy of the optical photon and be elevated into the higher energy state. If the Fermi level is slightly lowered so that there are fewer electrons available in this ground state, then the strength of the optical absorption will be lowered. One such way to create an electric field near the surface of a nanotube is to use free charges in a solution, such as an electrolyte [References 3 and 4]. In this situation the free charge may be driven to the nanotube surface by an external electric field [Reference 3] to modify the Fermi level. Another means is to vary the strength of the electrolyte by using electrolytes of differing ph values [Reference 4].

A variation of the embodiment uses fluorescence of the nanotubes rather than absorption characteristics. That variation uses the fact that carbon nanotubes have been found to fluoresce brightly [Reference 11] undergoing a process termed direct bandgap fluorescence. In this process light is absorbed at the S22 transition wavelength and the nanotube sheds the absorbed light energy by emitting a light photon at the S11 wavelength. Since transitions between van Hove singularities are involved similar to the discussions above, this process is termed direct bandgap fluorescence and can be very efficient. More typically in conventional fluorescence, emission follows a complicated path to de-excitation that leads to the emission of a fluorescence photon with some degree of probability, and is therefore much less efficient. Since the ratio between light at the S22 and S11 wavelengths is measured, the variation is also amplitude independent.

It must be emphasized that in all of the sensors concepts to be disclosed in this patent disclosure based on carbon nanotubes, that carbon nanotubes have been found to be almost totally immune to even extremely high levels of electromagnetic interference, EMI, which is a major requirement of these sensors [References 1 and 2]. Carbon nanotubes, even the semiconducting types that are being employed in this disclosure, demonstrate the remarkable property that they completely shunt external sources of electric field. This has been found to be true for external sources of electric field up to hundreds and perhaps even thousands of millions of volts per meter. The Air Force has an EMI immunity requirement that devices need to withstand fields on the order of several million volts per meter, so nanotubes surpass this requirement by many orders of magnitude. This is a very important advantage for carbon nanotubes in this application, as no other technology is known that has this remarkable and critical property.

Throughout the present disclosure, the prior art is discussed with reference to the following references:

Reference 1: L. Lou, P. Nordlander and R. E. Smalley "Fullerene nanotubes in electric fields", *Physical Review B*, Volume 52, Number 3, 15 Jul. 1995, pages 1429-1432

Reference 2: Alain Rochefort, Massimiliano Di Ventra, and Phadeon Avouris "Switching behavior of semiconducting carbon nanotubes under an external electric field", *Applied Physics Letters*, Volume 78, Number 17, 23 Apr. 2001, pages 2521-2523

Reference 3: Sami Rosenblatt, Yuval Yaish, Jiwoong Park, Jeff Gore, Vera Sazonova, and Paul L. McEuen, "High performance electrolyte-gated carbon nanotube transistors", *Nano Letters* 2, 869 (2002)

Reference 4: Wei Zhao, Chulho Song, and Pehr E. Pehrsson, "Water-Soluable and Optically pH-Sensitive Single-Walled Carbon Nanotubes from Surface Modification", *Journal of the American Chemical Society*, Volume 124, Number 42, 2002, pages 12418-12419

Reference 5: Axel Hagen and Tobias Hertel "Quantitative Analysis of Optical Spectra from Individual Single-Wall Carbon Nanotubes", *Nano Letters*, 3, 383 (2003)

Reference 6: M. S. Dresselhaus, G. Dresselhaus, and Ph. Avouris (Editors) "Carbon Nanotubes Synthesis, Structure, Properties and Applications" Topics in Applied Physics Volume 80, Springer-Verlag Berlin Heidelberg Germany 2001, ISBN 3-540-41086-4

Reference 7: Shu Peng et. al. "Carbon Nanotube Chemical and Mechanical Sensors", Conference Paper for the 3$^{rd}$ International Workshop on Structural Health Monitoring Reference 8: C. Kilic et. al. "Variable and reversible quantum structures on a single carbon nanotube", *Condensed Matter* 0011309 v1, 17 Nov. 2000

Reference 9: O. Gulseren et. al. "Reversible Band Gap Engineering in Carbon Nanotubes by Radial Deformation", *Condensed Matter* 0203226 v1, 11 Mar. 2002

Reference 10: S. Peng and K. Cho "Nano Electro Mechanics of Semiconducting Carbon Nanotube", *Journal of Applied Mechanics*, Volume 69, July 2002, pages 451-453

Reference 11: Michael J. O'Connell et. al. "Band Gap Fluorescence from Individual Single-Walled Carbon Nanotubes", *Science* Volume 297, 26 Jul. 2002, Pages 593-596.

BRIEF DESCRIPTION OF THE DRAWINGS

Two preferred embodiments of the present invention will be set forth in detail with reference to the drawings, in which:

FIG. 1 is a graph showing the optical absorption wavelength of a nanotube versus the degree of deformation;

FIG. 2 is a schematic diagram showing a sensor according to the first preferred embodiment, which exploits the phenomenon of FIG. 1;

FIG. 3 is a graph showing a density of states in nanotubes and in particular showing transitions between van Hove singularities;

FIG. 4 is a pair of graphs showing optical absorption modulation of nanotubes due to Fermi level modulation; and FIG. 5 is a schematic diagram showing a sensor according to the second preferred embodiment, which exploits the phenomena of FIGS. 3 and 4.

DETAILED DESCRIPTION OF THE PREFERRED EMBODIMENTS

Two preferred embodiments of the present invention will be set forth in detail with reference to the drawings, in which like reference numerals refer to like elements throughout.

A first preferred embodiment will now be set forth with reference to FIGS. 1 and 2. FIG. 1 shows the optical absorption spectrum of a carbon nanotube as a function of the degree of deformation. The left column shows various states of deformation, from no deformation at all (top) to extreme deformation (bottom). The right column shows the absorption spectrum for each degree of deformation. The notch, indicating the optical absorption wavelength, moves to the left, indicating absorption at lower wavelengths, as the deformation decreases.

FIG. 2 shows a magnetic field sensor 200 based on this effect. The parameter to be measured is converted into a physical compression on a nanotube film 202 on an optical surface. In the case of the magnetic field sensor 200, a magnetostrictive material 204 such as Terfenol-D is used to create this compressive force, represented in FIG. 2 as a strain vector V, as a function of the strength of the magnetic field. This compressive force flattens the nanotubes in the film 202 to a certain degree, and this in turn shifts the wavelength at which the nanotubes absorb light.

The nanotube film 202 is disposed between two optical elements 206, 208, which define a cavity 210 between them. In a transmissive embodiment, each of the optical elements 206, 208 has a first optical face 212 facing the cavity 210, a second optical face 214 not facing the cavity, and an internal, 45-degree reflector 216. The second optical face 214 in each optical element 206, 208 is an input or output port for input light $L_I$ or output light $L_O$ and can be connected to an optical fiber (not shown) or the like as needed. Within each optical element 206, 208, the reflector 216 defines an optical path between the first and second optical faces 212, 214.

Input light $L_I$ enters the first optical element 206 and is directed through the nanotube film 202. The force applied by the magnetostrictive material 204 causes a shift in the optical absorption wavelength, as explained above and shown in FIG. 1. Thus, a spectrum of the output light $L_O$ has a notch at the shifted optical absorption wavelength, caused by absorption of light at that wavelength by the nanotube film 202. An analysis of the spectrum of the output light $L_O$ allows an easy determination of the location of the notch and thus of the shift in the optical absorption wavelength. That shift in turn allows a determination of the amount of force applied and thus the physical quantity to be sensed (in this case, the magnetic field).

For this sensor concept, we do not need anything close to total bandgap closure as discussed in the above research reports. We need only a very small, but measurable amount of shift in the nanotube optical absorption wavelength that falls within the wavelength bandwidth of a typical WDM channel. A change in the optical absorption wavelength on the order of nanometers or perhaps up to tens of nanometers would be sufficient. This amounts to a compression of the nanotubes by only on the order of one or two percent at most. It has been calculated based on the published compressive modulus of carbon nanotubes that this compressive force can easily be attained in practice.

This technique achieves light amplitude independence in the following way. The information regarding the parameter being measured resides in the point at which the nanotube absorbs light and this can be measured in a number of ways. As long as the logic making the determination of the measured parameter has enough light to detect and adequately determine the wavelength at which the nanotube is absorbing, then the measurement can be made. As the light amplitude gets larger or smaller the wavelength at which the nanotube absorbs does not change and the way to measure this can be done on an amplitude independent manner as is well known in the art.

Any parameter that can be converted into a compressive force on the nanotubes can be measured by this technique. Current can be measured by using the fact that a current gives rise to a magnetic field, as is often done in current measuring sensors, and then measuring the magnetic field as described above. Temperature can be measured by utilizing a material that changes dimensions with temperature, as many materials do to a large degree. This dimensional change is then used to affect a compressive force on the nanotubes. Voltage can be measured by utilizing a piezoelectric material to convert voltage into a dimensional change of a material and likewise affect a compressive force on the nanotubes.

A second preferred embodiment will now be set forth with reference to FIGS. 3-5. The optical transition between the first pair of van Hove singularities, termed S11 in FIG. 3, may be strengthened or weakened by altering the Fermi level [Reference 4]. This is because the electrons in the ground state of this particular optical transition are very near the Fermi level to start with. If the Fermi level is changes, a greater number of electrons may be available, which strengthens the optical absorption, or a fewer number of electrons may be available, which weakens the optical absorption strength. This phenomenon is shown in FIG. 4, which is excerpted from the work of Zhao in Reference 4.

The interesting thing to note is that it is only the strength of the first optical transition, S11, that is modified by altering the Fermi level. The strength of the second optical transition, designated S22 in FIG. 3, is not affected at all, as can be seen in FIG. 4. This is because the electrons in the ground state of transition S22 are far away from the Fermi level and a modulation of the Fermi level does not alter the number of electrons available for this optical transition. The ratio of the strength of the S11 to S22 optical transitions as a function of the pH of the electrolyte is very linear.

A sensor based on this phenomenon is shown in FIG. 5 as 500. The general approach is that the parameter to be measured causes the Fermi level to be changed. The sensor 500 of FIG. 5, like the sensor 200 of FIG. 2, has optical elements 206 and 208 and a nanotube film 202. However, the optical elements 206 and 208 define between them a cavity 510 containing not only the nanotube film 202, but also an electrolyte, semiconductor or other material 520 for creating a free charge, the material 520 being connected to a voltage 522 to be measured.

In the case of FIG. 5, it is voltage 522 that is being measured that creates an electric field that drives charge either to or away from the nanotube surface, depending on the direction of the electric field and the sign of the free charge. The material 520 used to create the available free charge may be an electrolyte as in References 3 and 4, or it may be a semiconductor material in close proximity or even coating the nanotube. The charge may be generated by a material near the nanotube through a very thin layer of dielectric material, such as the so called "high k" dielectric materials, where k stands for the dielectric constant of the material. High k, and even super-high k dielectric materials are being pursued in nanotube research because the electric field must be generated very near the nanotube surface to be effective. It has been found that normal dielectric materials break down when the very thin layers needed to get the charge near the nanotube surface are employed.

The sensor measurement technique that achieves light amplitude independence is to use the ratio of the received light signal at two wavelengths, where one wavelength is centered at the S11 transition and the other is centered at the S22 transition. As long as the ratio is used to compute the value of the parameter being measured, the optical losses through connectors and the like will be the same for both wavelengths, and the ratio will be unaffected by these losses. Thus, the detection is independent of light amplitude.

A variation of the sensor 500 uses the fact that carbon nanotubes have been found to fluoresce brightly [Reference 11] undergoing a process termed direct bandgap fluorescence. In this process light is absorbed at the S22 transition wavelength and the nanotube sheds the absorbed light energy by emitting a light photon at the S11 wavelength. Since transitions between van Hove singularities are involved similar to the discussions above, this process is termed direct bandgap fluorescence and can be very efficient. More typically in conventional fluorescence, emission follows a complicated path to de-excitation that leads to the emission of a fluorescence photon with some degree of probability, and is therefore much less efficient.

Therefore a variant of the above sensor design can be disclosed that utilizes fluorescence instead of absorption at the two bands, S11 and S22. The sensor design utilizing fluorescence would be diagramed the same as the sensor 500 of FIG. 5. In the first technique, two light sources are needed. One light source is centered at the wavelength of absorption band S11 and the other is centered at the wavelength of absorption band S22. The ratio of the received light is indicative of the parameter being measured.

In this second approach using direct bandgap fluorescence, only one light source is needed, and this is the main advantage of this approach. This light source is centered at the wavelength of absorption band S22. At the receiver end of the fiber, light is still detected at both wavelengths corresponding to S11 and S22. Now the light received at wavelength S11 is due to fluorescence from the nanotubes, which act like light sources in effect. Determining the ratio of light power received at both wavelengths S22 and S11 still remains the basis for making a determination of the parameter being measured by the sensor. In this case the strength of the fluorescence will follow the amount of light power receive at the nanotubes at the S22 wavelength, so the ratio of the light power received at the two wavelengths is still a light amplitude independent manner of making a measurement of a parameter. All optical losses downstream of the nanotube sensor will be in common with both S22 and S11 wavelengths as well, so that light amplitude independent operation is maintained.

While two preferred embodiments have been set forth in detail above, those skilled in the art who have reviewed the present disclosure will readily appreciate that other embodiments can be realized within the scope of the present invention. For example, any wavelength-dependent change in the absorption of the nanotubes can be detected and used in a sensor, which would still operate independently of light amplitude. Moreover, the sensor can be either transmissive or reflective; in the latter case, one of the optical elements is a mirror. Therefore, the present invention should be construed as limited only by the appended claims.

I claim:

1. A method for causing a semiconducting carbon nanotube material to act as a passive sensor of a physical quantity, the method comprising:
   (a) controlling the semiconducting carbon nanotube material in accordance with the physical quantity to cause a change to an optical absorption or reflection characteristic of the semiconducting carbon nanotube material which depends on light wavelength but not on light amplitude;
   (b) applying light to the semiconducting carbon nanotube material;
   (c) receiving the light which has been applied to the semiconducting carbon nanotube material;
   (d) determining the change to the optical absorption or reflection characteristic from the light receive in step (c); and
   (e) determining the physical quantity from the change determined in step (d).

2. The method of claim 1, wherein the optical absorption or reflection characteristic is an optical absorption wavelength.

3. The method of claim 2, wherein step (a) comprises:
   (i) converting the physical quantity to a mechanical force; and
   (ii) using the mechanical force to compress the semiconducting carbon nanotube material to change the optical absorption wavelength.

4. The method of claim 3, wherein step (a)(i) comprises applying the physical quantity to a material which undergoes elongation in response to the physical quantity.

5. The method of claim 4, wherein the physical quantity is a magnetic field, and wherein the material which undergoes the elongation comprises a magnetostrictive material.

6. The method of claim 5, wherein the magnetostrictive material comprises Terfenol-D.

7. The method of claim 4, wherein the physical quantity is voltage, and wherein the material which undergoes elongation comprises a piezoelectric material.

8. The method of claim 4, wherein the physical quantity is electrical current, wherein the material which undergoes the elongation comprises a magnetostrictive material, and wherein step (a) comprises generating a magnetic field from the electrical current and applying the magnetic field to the magnetostrictive material.

9. The method of claim 8, wherein the magnetostrictive material comprises Terfenol-D.

10. The method of claim 4, wherein the physical quantity is temperature, and wherein the material which undergoes elongation is a material which undergoes elongation in accordance with the temperature.

11. The method of claim 1, wherein the optical absorption or reflection characteristic is a ratio of optical absorption at a first wavelength to an optical absorption at a second wavelength.

12. The method of claim 11, wherein step (a) comprises:
   (i) generating an electric charge in accordance with the physical quantity; and
   (ii) exposing the semiconducting carbon nanotube material to the electric charge to change the ratio.

13. The method of claim 12, wherein the physical quantity is voltage, and wherein step (a)(i) comprises applying the voltage to a material which generates the electric charge.

14. The method of claim 13, wherein the material which generates the electric charge comprises an electrolyte.

15. The method of claim 13, wherein the material which generates the electric charge comprises a semiconductor.

16. The method of claim 1, wherein the optical absorption or reflection characteristic is a ratio of optical absorption at a first wavelength to a fluorescence at a second wavelength.

17. The method of claim 16, wherein step (a) comprises:
   (i) generating an electric charge in accordance with the physical quantity; and
   (ii) exposing the semiconducting carbon nanotube material to the electric charge to change the ratio.

18. The method of claim 17, wherein the physical quantity is voltage, and wherein step (a)(i) comprises applying the voltage to a material which generates the electric charge.

19. The method of claim 18, wherein the material which generates the electric charge comprises an electrolyte.

20. The method of claim 18, wherein the material which generates the electric charge comprises a semiconductor.

21. A passive optical sensor for sensing a physical quantity, the passive optical sensor comprising:
   a semiconducting carbon nanotube material having an optical absorption or reflection characteristic which depends on light wavelength but not on light amplitude;
   first and second optical elements for defining a cavity in which the semiconducting carbon nanotube material is disposed, for transmitting light to the semiconducting carbon nanotube material, and for transmitting light which has been made incident on the semiconducting carbon nanotube material; and
   a controlling element for controlling the semiconducting carbon nanotube material in accordance with the physical quantity to cause a change to the optical absorption or reflection characteristic of the semiconducting carbon nanotube material which depends on light wavelength but not on light amplitude.

22. The sensor of claim 21, wherein the optical absorption or reflection characteristic is an optical absorption wavelength.

23. The sensor of claim 22, wherein the controlling element converts the physical quantity to a mechanical force and uses the mechanical force to compress the semiconducting carbon nanotube material to change the optical absorption wavelength.

24. The sensor of claim 23, wherein the controlling element comprises a material which undergoes elongation in response to the physical quantity.

25. The sensor of claim 24, wherein the physical quantity is a magnetic field, and wherein the material which undergoes the elongation comprises a magnetostrictive material.

26. The sensor of claim 25, wherein the magnetostrictive material comprises Terfenol-D.

27. The sensor of claim 24, wherein the physical quantity is voltage, and wherein the material which undergoes elongation comprises a piezoelectric material.

28. The sensor of claim 24, wherein the physical quantity is electrical current, wherein the material which undergoes the elongation comprises a magnetostrictive material, and wherein step (a) comprises generating a magnetic field from the electrical current and applying the magnetic field to the magnetostrictive material.

29. The sensor of claim 28, wherein the magnetostrictive material comprises Terfenol-D.

30. The sensor of claim 24, wherein the physical quantity is temperature, and wherein the material which undergoes elongation is a material which undergoes elongation in accordance with the temperature.

31. The sensor of claim 21, wherein the optical absorption or reflection characteristic is a ratio of optical absorption at a first wavelength to an optical absorption at a second wavelength.

32. The sensor of claim 31, wherein the controlling element generates an electric charge in accordance with the physical quantity and exposes the semiconducting carbon nanotube material to the electric charge to change the ratio.

33. The sensor of claim 32, wherein the physical quantity is voltage, and wherein the controlling element comprises a material which generates the electric charge in response to the voltage.

34. The sensor of claim 33, wherein the material which generates the electric charge comprises an electrolyte.

35. The sensor of claim 33, wherein the material which generates the electric charge comprises a semiconductor.

36. The sensor of claim 21, wherein the optical absorption or reflection characteristic is a ratio of optical absorption at a first wavelength to a fluorescence at a second wavelength.

37. The sensor of claim 36, wherein the controlling element generates an electric charge in accordance with the physical quantity and exposes the semiconducting carbon nanotube material to the electric charge to change the ratio.

38. The sensor of claim 37, wherein the physical quantity is voltage, and wherein the controlling element comprises a material which generates the electric charge in response to the voltage.

39. The sensor of claim 38, wherein the material which generates the electric charge comprises an electrolyte.

40. The sensor of claim 38, wherein the material which generates the electric charge comprises a semiconductor.

* * * * *